US00PP37060P2

(12) United States Plant Patent
Wu

(10) Patent No.: US PP37,060 P2
(45) Date of Patent: Oct. 21, 2025

(54) BERMUDAGRASS PLANT NAMED 'OSU2082'

(50) Latin Name: ***Cynodon transvaalensis* Burtt-Davy x *Cynodon dactylon Pers.***
Varietal Denomination: OSU2082

(71) Applicant: THE BOARD OF REGENTS FOR THE OKLAHOMA AGRICULTURAL AND MECHANICAL COLLEGES, Stillwater, OK (US)

(72) Inventor: Yanqi Wu, Stillwater, OK (US)

(73) Assignee: BOARD OF REGENTS FOR THE OKLAHOMA AGRICULTURAL AND MECHANICAL COLLEGES, Stillwater, OK (US)

( * ) Notice: Subject to any disclaimer, the term of this patent is extended or adjusted under 35 U.S.C. 154(b) by 0 days.

(21) Appl. No.: 18/923,387

(22) Filed: Oct. 22, 2024

(51) Int. Cl.
*A01H 5/12* (2018.01)
*A01H 6/46* (2018.01)

(52) U.S. Cl.
USPC ..... Plt./389
CPC ..... *A01H 6/46* (2018.05)

(58) Field of Classification Search
USPC ..... Plt./389
CPC ..... A01H 5/12
See application file for complete search history.

(56) References Cited

PUBLICATIONS

U.S. Appl. No. 18/923,354, filed Oct. 22, 2024, 12 pages.

*Primary Examiner* — Kent L Bell
(74) *Attorney, Agent, or Firm* — McKee, Voorhees & Sease, PLC

(57) ABSTRACT

'OSU2082' is disclosed as a new clonally propagated F1 hybrid turf Bermudagrass cultivar which performs exceptionally well in severe drought conditions. It does not produce frequent seed heads. The variety demonstrates excellent establishment characteristics and leaf spot disease resistance, with fine leaf texture, and sufficient sod tensile strength for reliable, large scale commercial production on farms.

4 Drawing Sheets

GOVERNMENT SUPPORT

This invention was made in part with government support under United States Department of Agriculture SCRI Grant Nos. SCRI-2019-1455-05 and 2019-51181-30472 The government has certain rights in this invention.

Botanical designation: Genus and species: *Cynodon transvaalensis* Burtt-Davy x *Cynodon dactylon* Pers.

Cultivar denomination: The new plant has the cultivar denomination 'OSU2082'.

SUMMARY

This disclosure relates to a new and distinct cultivar of bermudagrass designated 'OSU2082' and botanically known as *Cynodon transvaalensis* Burtt-Davy x *Cynodon dactylon* Pers. 'OSU2082' is a high quality interspecific, turf-type, F1 bermudagrass hybrid. It has been clonally propagated and has exhibited a significantly improved drought resistance in a wide range of the southern United States. It has performed exceptionally well in severe drought conditions in California, Oklahoma, and Texas. It does not produce frequent seedheads. It has demonstrated excellent establishment characteristics and leaf spot disease resistance, fine leaf texture, and sufficient sod tensile strength for reliable, large scale commercial production on farms.

DETAILED BOTANICAL DESCRIPTION

Description, Origin, and History

Figure 1:
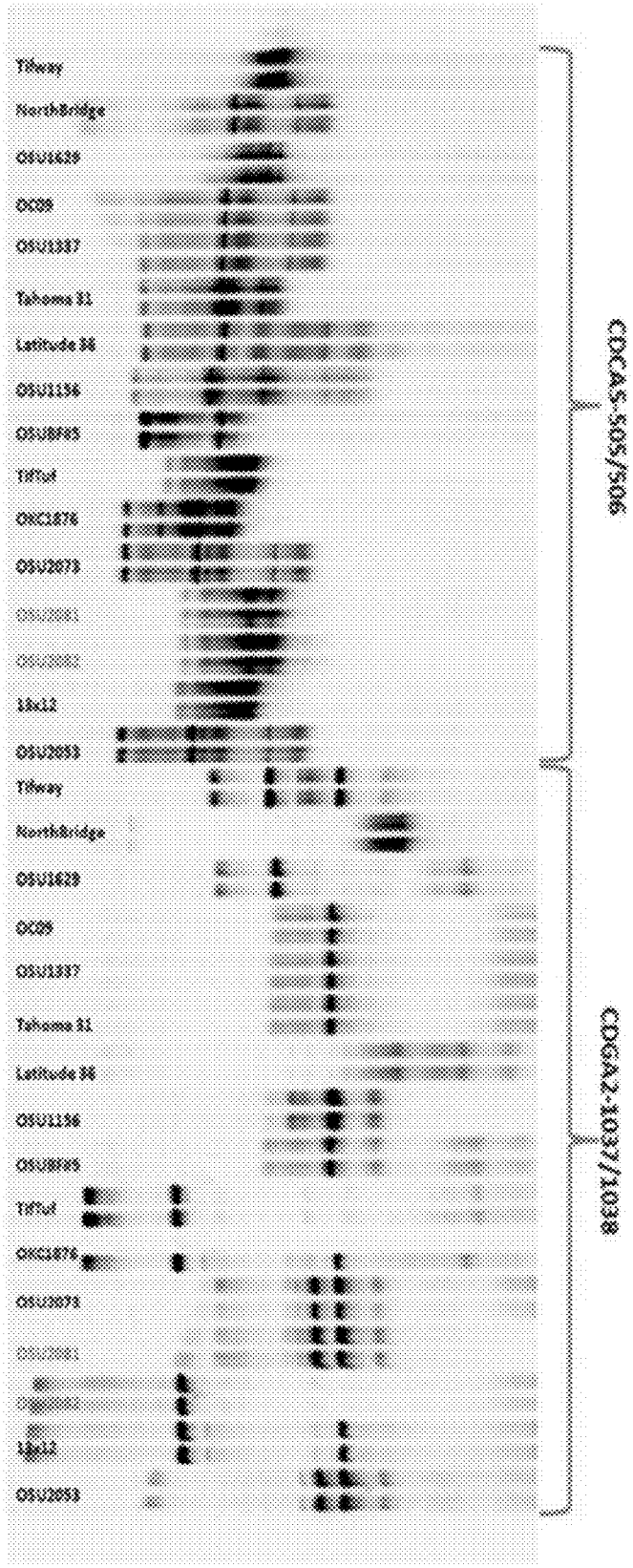
FIG. 1 is a simple sequence repeat DNA band patterns amplified by two primer pairs, CDCA5-505/506 (the gel image on the left) and CDGA2-1037/1038 (on the right) showing 'OSU2081' and 'OSU2082' are distinct genotypes from other entities including 'Tifway', 'NorthBridge', 'Tahoma 31', 'Latitude 36', 'TifTuf' and 'OKC1876'.

'OSU2082' is a vegetatively propagated F1 hybrid derived from a cross between *C. transvaalensis* selection '2747' (not patented) and *C. dactylon* var. *dactylon* African bermudagrass accession 'A10202' (not patented). In 2018, a small crossing plot was established by planting clonal plants of the two parents in proximity in Stillwater, Oklahoma. Mature seedheads were hand-harvested from the African bermudagrass accession 'A10202' in the crossing block in summer 2019. Seedlings from the harvested seeds of this cross along with seedlings from other crosses were screened for leaf texture and color, and rooting potential in a greenhouse in Stillwater, Oklahoma in the winter between 2019 and 2020. The two grasses have been included in subsequent multiple tests at Stillwater, Oklahoma, and locations in California, Texas, Georgia, Florida, and North Carolina since 2020. 'OSU2082' is sexually sterile and must be propagated vegetatively. It has been clonally propagated through many seasons in Stillwater, Oklahoma. The cultivar is stable, with advanced generation clonal plants reproducing true to type. 'OSU2082' is sexually sterile, whereas both parents, '2747' and 'A10202', are sexually fertile.

The foliage of 'OSU2082' is green (RHS 144B, The Royal Horticultural Society Colour Chart, 6th edition (2015)). The rhizome is a yellowish white (RHS 158C); the stolon is a moderate yellow green (RHS 146D); in summer, both the upper and lower leaf blade surfaces are strong yellow green (RHS 144B); in winter, both the upper and lower leaf blade surfaces are a strong yellow (RHS 153D); the leaf sheath is light yellowish green (RHS 144D); the collar is greenish white (RHS 157D); the lemma, palea and culm are light yellowish green (RHS 145D). 'OSU2082' is sterile so there is no seed for observation.

The rhizome measures 130 mm long and 1.2 mm in diameter on average. The average stolon length and diameter is 160 mm and 1 mm, respectively. The internode length averages 25 mm and internode diameter averages 1 mm. The length and width of the leaf blade are 39 mm and 1.97 mm, respectively, on average. The observed length and diameter of leaf sheath are 12 mm and 1 mm, respectively, on average. The observed length of the ligule is 1.5 mm on average. An observed inflorescence has 3 racemes, and each raceme is approximately 21 mm in length. The observed length of the spikelet, glume, palea, lemma, peduncle, and culm is 2 mm, 1 mm, 2 mm, 1.8 mm, 80 mm, and 120 mm, respectively, on average.

'OSU2082' typically grows laterally with solons, and vertically and obliquely via stems. This grass can form a relatively dense sod if mowed or trimmed regularly.

'OSU2082' has a flat, linear leaf blade with a sharp but soft apex. Its leaf blade margin is smooth. Its leaf blade becomes wider towards its base. Its leaf blade bears tiny, sparse silver-colored hair on the upper surface while its lower surface is smooth. Its leaf sheath is smooth. 'OSU2082' has a hairy ligule. Its auricle is short and round. Its collar is narrow. Its bud is folded in leaf blades. The inflorescence is digitated in a whorl. Each raceme bears 18-22 spikelets. One spikelet contains one floret. Typically, 'OSU2082' flowers from late spring to early summer. 'OSU2082' has a dark purple stigma and is approximately 0.7 mm in length. Its anthers are light purple and 1.0-1.3 mm long.

DNA Profiling Experiments

Figure 2:
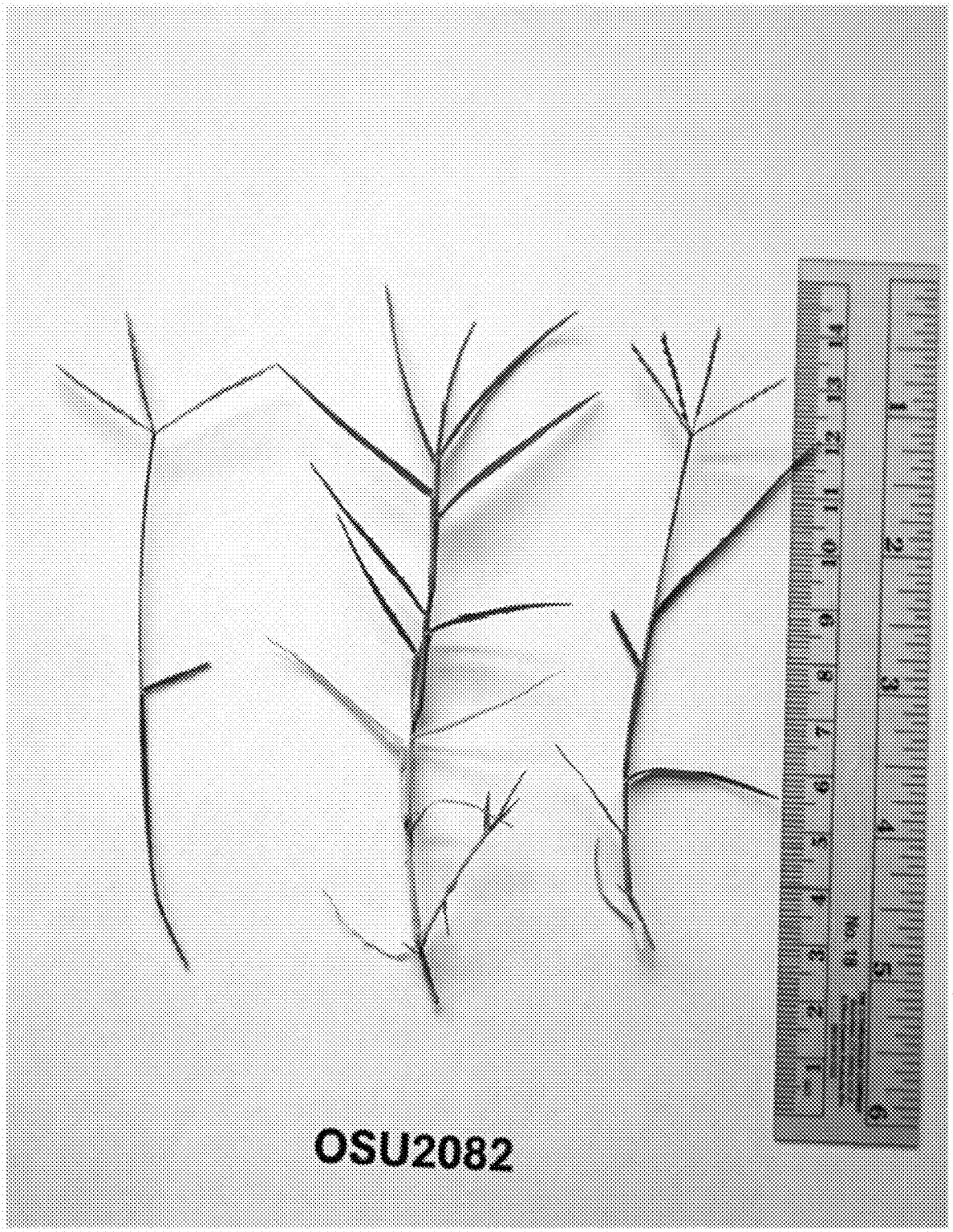
FIG. 2 is a photograph of inflorescences and leaves of variety 'OSU2082' taken on Aug. 6, 2024, at Stillwater OK of plants one year old.
Figure 3:
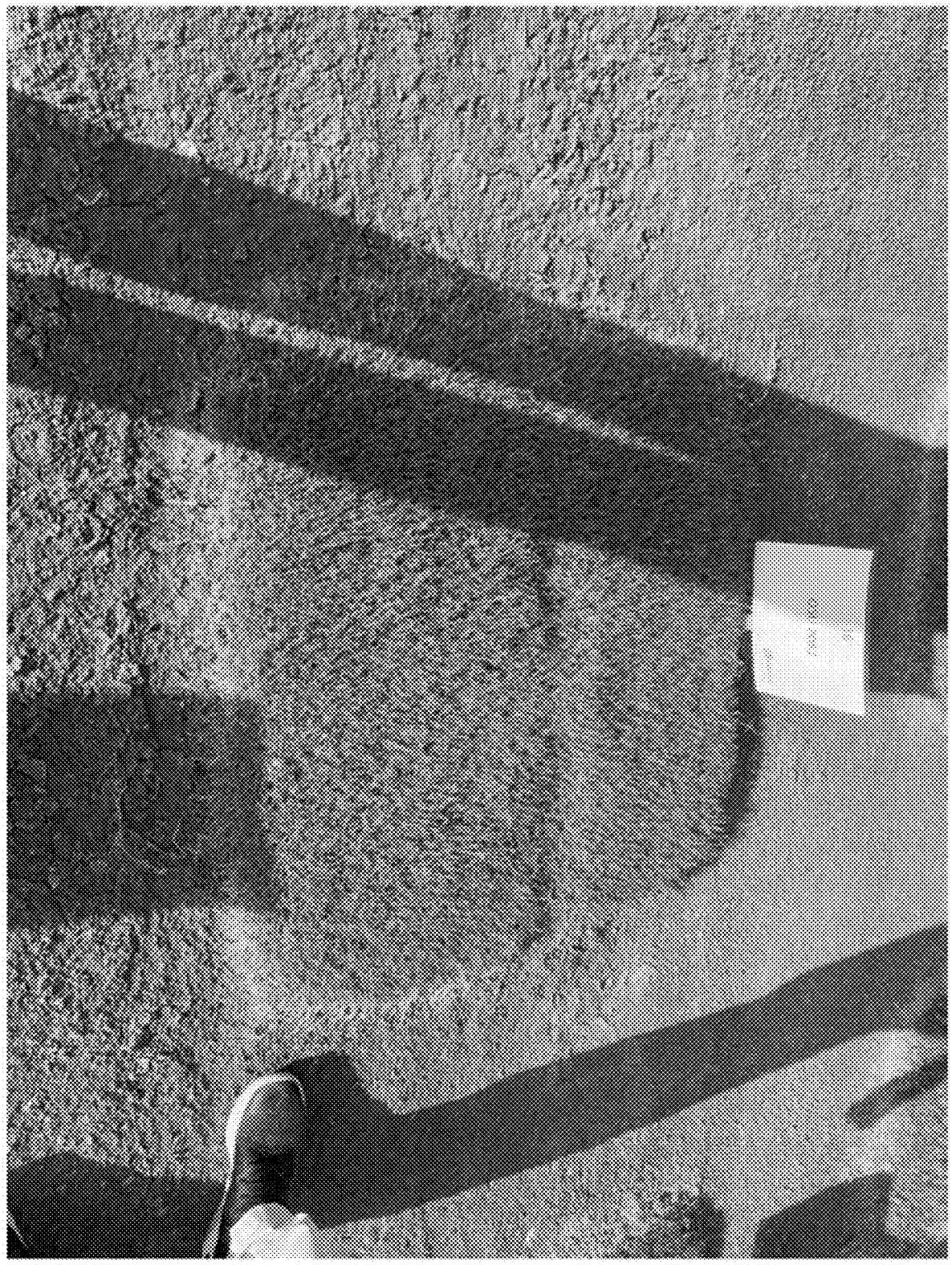
FIG. 3 is a photograph of variety 'OSU2082' taken on Sep. 20, 2022 at Riverside, CA of plants 2 years old under salinity conditions of 4.4 dS $m^{-1}$.
Figure 4:
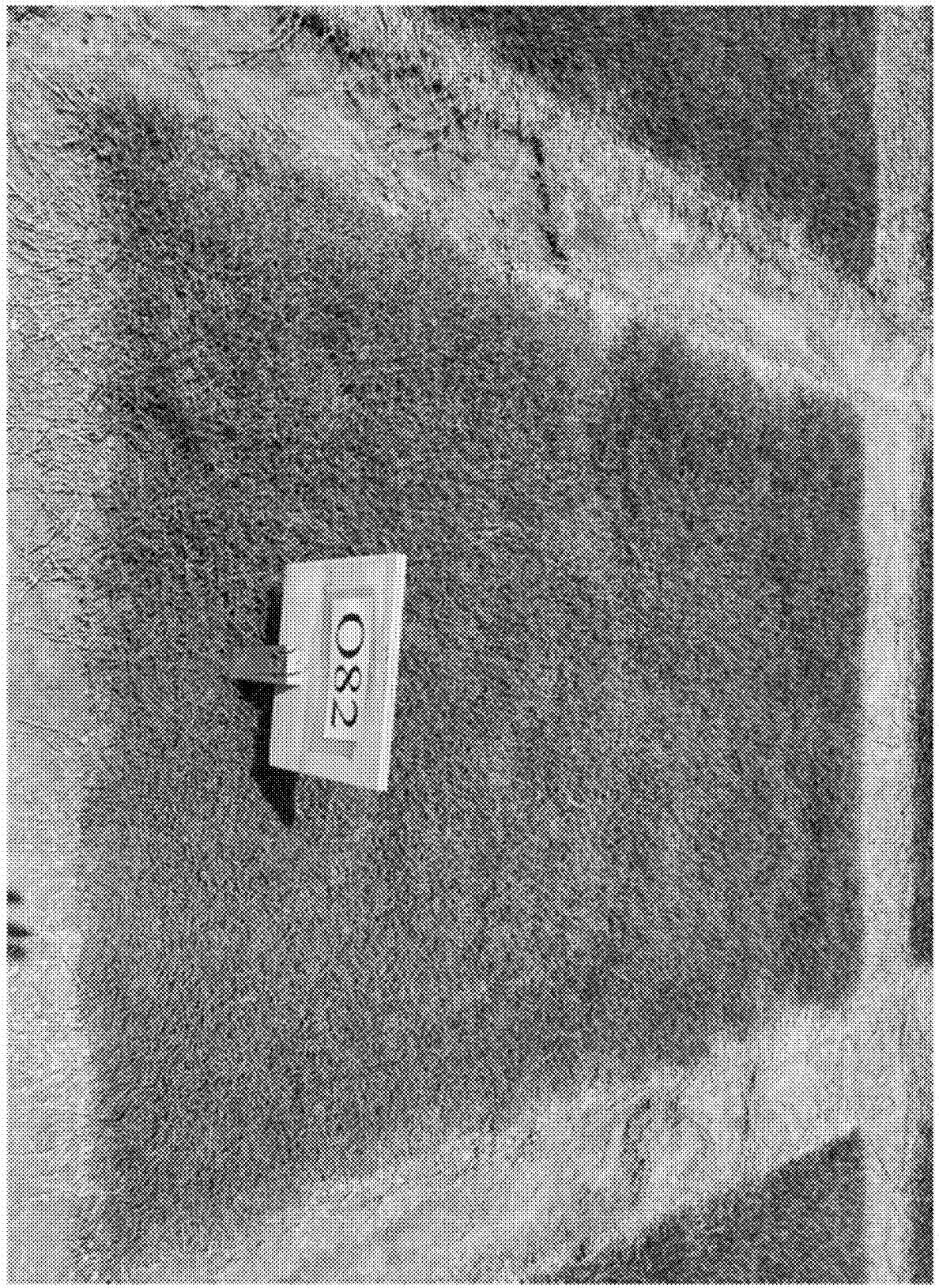
FIG. 4 is a photograph of a plot of variety 'OSU2082' (abbreviated as "O82" in photograph) taken at Stillwater, OK on May 22, 2022 of 2 year old plants.

Simple sequence repeat (SSR) marker experiments definitively indicated that 'OSU2082' is a unique genotype, distinct from 11 popular cultivars as well as variety 'OSU2081' (FIGS. 1 and 2, respectively).

Morphological Characteristics and Performance

A greenhouse experiment including three experimental entries ('OSU2082', 'OSU1337' (not patented), and 'OSU2073' (not patented)) and two cultivars ('Tahoma 31' (experimental name 'OKC 1131', U.S. Plant Pat. No. 31,695) and 'TifTuf' (experimental name 'DT-1', U.S. Plant Pat. No. 27,392)) were planted in 12-inches pots in a randomized complete block design with three replications in Stillwater, Oklahoma in July 2023. Twenty stems per pot were randomly collected in December 2023 and mean values per replication were used in the data analysis. The width of the first leaf blade on the second node of 'OSU2082' was not different from that of 'TifTuf' but was wider than that of 'Tahoma 31' (Table 1). The length of the leaf blade of 'OSU2082' was not different from that of 'TifTuf', but longer than that of 'Tahoma31'. The length of the second internode of 'OSU2082' was not different from that of 'TifTuf', but much longer than that of 'Tahoma 31'. The internode diameter of 'OSU2082' was the same as that of 'TifTuf' and 'Tahoma 31'.

TABLE 1

Measurements of leaf blades and stolons in turf bermudagrass grown in greenhouse in 2023.

| Entry | LW (mm)§ | LL (mm) | SIL (mm) | SID (mm) |
|---|---|---|---|---|
| OSU1337 | 1.67 | 25.57 | 10.87 | 0.57 |
| OSU2073 | 2.00 | 30.50 | 15.77 | 0.60 |
| OSU2082 | 1.97 | 39.10 | 25.30 | 0.63 |
| Tahoma31 | 1.77 | 21.73 | 9.93 | 0.63 |
| TifTuf | 2.00 | 51.63 | 23.73 | 0.63 |
| LSD0.05 | 0.15 | 12.85 | 4.81 | 0.11 |

LW = leaf blade width (mm) on the first leaf on the second node LL == leaf blade length (mm) on the first leaf on the second node SIL = second shoot internode length (mm) SID = second shoot internode diameter (mm)

Salinity Tolerance Test

A field experiment to assess bermudagrass response to saline water was conducted at Riverside, CA. The study had 35 experimental entries, including 'OSU2081' (U.S. Plant patent application Ser. No. 18/923,354) and 'OSU2082', and three cultivars ['Santa Ana' (salt tolerant standard) (not patented), 'TifTuf' (drought resistant standard), and 'Tifway' (a widely used commercial standard) (not patented)]. Plots were planted in the center of 3 ft by 3 ft plots in a randomized complete block design with three replicates in 2020. From 2021 to 2023, the trial was irrigated from July to October (dry season) with saline water (4.4 dS m−1) at 75% reference evapotranspiration (ET0) replacement. Data presented here included experimental entries and the standard cultivars.

When data were averaged across years (Table 2), 'OSU2081' and 'OSU2082' exhibited establishment cover rates (%) greater than 'Santa Ana', but no difference from the other two standards. The response of 'OSU2081' to mites (*Eriophyes cynodoniensis*) was similar to the three cultivars. 'OSU2082' was more resistant to mites than 'Tifway'. 'OSU2081' had improved fall color retention as compared to 'Tifway', but no difference from 'TifTuf' and 'Santa Ana'. 'OSU2082''s fall color retention was not different from the three standards. 'OSU2081' and 'OSU2082' produced similar amounts of inflorescences compared to Santa Ana, but more inflorescences than 'TifTuf' and 'Tifway' under no saline water irrigation. There is no difference in inflorescence prolificacy among 'OSU2081' and 'OSU2082' and the three standards under saline water irrigation. 'OSU2081' and 'OSU2082''s spring green-up was similar to the three cultivars. Their turfgrass quality ratings were improved over 'Tifway''s under no-saline water irrigation. Under saline water irrigation, their turfgrass quality was not different from the three cultivars.

TABLE 2

Turf bermudagrass performance in a saline-water irrigated trial at Riverside, CA for 2020-2023.

| Entry | Cover (%) | Mite Injury& | Fall color | Inflorescence¶ No S¥ | Inflorescence¶ S |
|---|---|---|---|---|---|
| OSU2018 | 70.4 | 5.3 | 5.4 | 4.3 | 3.8 |
| OSU2022 | 92.1 | 5.3 | 6.7 | 2.8 | 4.8 |
| OSU2034 | 88.8 | 6.3 | 6.7 | 1.2 | 3.7 |
| OSU2035 | 84.2 | 7.0 | 6.0 | 4.3 | 3.1 |
| OSU2037 | 53.8 | 6.3 | 2.9 | 3.3 | 3.7 |
| OSU2039 | 50.4 | 5.7 | 5.0 | 3.1 | 3.1 |
| OSU2043 | 87.9 | 4.7 | 6.3 | 5.8 | 3.0 |
| OSU2066 | 90.0 | 8.0 | 6.8 | 6.8 | 2.9 |
| OSU2073 | 93.7 | 5.7 | 7.3 | 7.1 | 3.9 |
| OSU2074 | 75.8 | 6.0 | 1.6 | 2.9 | 3.6 |
| OSU2075 | 93.8 | 4.7 | 4.8 | 7.1 | 3.7 |
| OSU2083 | 93.3 | 6.0 | 7.8 | 5.8 | 2.8 |
| OSU2082 | 98.8 | 6.3 | 7.3 | 5.8 | 3.7 |
| OSU2088 | 81.3 | 6.0 | 6.9 | 7.7 | 3.3 |
| OSU2094 | 97.5 | 4.7 | 5.1 | 7.4 | 3.6 |
| OSU2101 | 93.8 | 5.7 | 6.7 | 5.8 | 4.2 |
| OSU2102 | 65.0 | 4.7 | 5.9 | 3.9 | 3.6 |
| SantaAna | 70.0 | 5.3 | 7.4 | 6.0 | 3.6 |
| TifTuf | 92.9 | 6.3 | 8.1 | 4.2 | 3.4 |
| Tifway | 90.4 | 4.3 | 6.0 | 3.8 | 3.7 |
| LSD0.05 | 9.8 | 1.7 | 1.7 | 1.2 | 2.2 |

| Entry | Re-covery | Spring greenup | Turfgrass quality# No S | Turfgrass quality# S |
|---|---|---|---|---|
| OSU2018 | 5.1 | 6.8 | 5.1 | 6.5 |
| OSU2022 | 5.1 | 5.9 | 5.6 | 5.3 |
| OSU2034 | 6.7 | 6.1 | 6.8 | 5.3 |
| OSU2035 | 5.4 | 5.9 | 6.5 | 5.9 |
| OSU2037 | 3.3 | 4.8 | 5.1 | 4.2 |
| OSU2039 | 4.1 | 4.8 | 4.7 | 4.4 |
| OSU2043 | 4.8 | 6.1 | 5.3 | 5.3 |
| OSU2066 | 5.4 | 5.3 | 6.1 | 5.3 |
| OSU2073 | 5.8 | 5.7 | 6.2 | 5.6 |
| OSU2074 | 3.0 | 2.6 | 4.4 | 5.2 |
| OSU2075 | 4.9 | 5.3 | 5.0 | 5.0 |
| OSU2083 | 6.0 | 6.0 | 5.2 | 5.8 |
| OSU2082 | 5.9 | 5.8 | 6.2 | 5.8 |
| OSU2088 | 5.3 | 5.1 | 5.4 | 5.4 |
| OSU2094 | 5.0 | 5.8 | 5.2 | 4.9 |
| OSU2101 | 4.8 | 6.2 | 5.6 | 5.1 |
| OSU2102 | 5.4 | 6.4 | 5.6 | 5.9 |
| SantaAna | 6.7 | 6.7 | 6.2 | 6.0 |
| TifTuf | 6.9 | 6.7 | 6.4 | 6.3 |
| Tifway | 5.3 | 5.3 | 5.4 | 5.8 |
| LSD0.05 | 1.0 | 1.7 | 0.7 | 0.5 |

Mite injury scale: 1-100% damage, 9 = no damage
Inflorescence abundance scale: 1 = no seedhead, 9 = maximum abundance
¥No S = no saline water irrigation, S = saline water irrigation
#is a scale, 1 = no wilting, 9 = fully wilting

Water Use Rate and Drought Response Test

A field experiment was carried out in Perkins, OK to measure water use and drought resistance. The study consisted of 8 bermudagrass entries, including 'OSU2082' (Table 3). The experiment was established in a randomized completed block design with 3 replicates in 2021. The water use trial was conducted under a rainout shelter between 23 June and 1 Sep. 2022. The total amount of water used to maintain 25% or less canopy wilt for 'OSU2082' was 1 inch (Table 3), which was not different from that of 'TifTuf' (1.7 inches), but significantly improved over 'Tahoma 31' (cold hardy, high water-use efficient standard) (4.3 inches), 'Tifway' (6.0 inches), and 'Latitude 36' (U.S. Plant Pat. No. 24,271) (cold hardy standard) (11.7 inches).

A drought test was conducted in the trial between 1 August and 10 Sep. 2023 for 40 days without rainfall and irrigation (Table 3). At the end of the dry-down period, 'OSU2082''s turfgrass quality rating (6.3) was the same as that of 'TifTuf' (6.3), significantly higher than 'Latitude 36' (2.0), 'Tifway' (3.7), and 'Tahoma 31' (4.3).

TABLE 3

Water use of bermudagrass entries during a 70-day drought period (June 23 to September 1) in 2022 and turf quality ratings after a 40-day acute drought period (August 1 to September 10) in 2023.

| Entry | Water use (inches)† in 2022 | Turf quality in 2023 |
|---|---|---|
| 'OSU2082' | 1.0 | 6.3 |
| 'OSU2094' | 2.3 | 6.3 |
| 'OSU1682' | 11.0 | 1.3 |
| 'TifB16117' | 0.3 | 6.0 |
| 'TifTuf' | 1.7 | 6.3 |
| 'Tahoma 31' | 4.3 | 4.3 |
| 'Tifway' | 6.0 | 3.7 |
| 'Latitude 361' | 1.7 | 2.0 |
| LSD 0.05 | 1.9 | 1.3 |

†One inch of water was applied to the plot once the canopy wilt reached 25% or higher.
‡Turf quality was rated at the end of a 40-day acute drought period on a 1-9 scale (1 = dead turf, 9 = ideal turf).

Regional Drought Resistance Test

This field trial [named Approach C in the 2019-2023 USDA Specialty Crop Research Initiative (SCRI) funded project] was conducted at 8 locations in the southern states (Stillwater, OK; Dallas, TX; Riverside, CA; Tifton and Griffin, GA; Jay and Citra, FL; and Jackson Springs, NC). The test included 34 experimental entries, including 'OSU2081' and 'OSU2082' and three standards ['TifTuf' (drought resistant standard), 'Tahoma 31' (cold hardy, high water-use efficient standard), and 'Tifway' (long-time, widely used standard)].

The nurseries were established using randomized complete block designs with 3 replications in 2020. Once the plots were fully established, the nurseries were not irrigated and managed under natural rainfall conditions. The establishment ratings were collected in 2020 and early 2021, while turf performance data were collected in 2021 to 2023.

'OSU2082' had an average cover (establishment rate %) lower than 'TifTuf', similar to 'Tahoma 31', but higher than 'Tifway' (Table 4). 'OSU2082' had a leaf spot disease resistance rating similar to 'TifTuf' and 'Tahoma 31', but more resistance than 'Tifway'. The fall color retention of 'OSU2082' was improved over 'Tahoma 31', but not different from that of 'TifTuf' and 'Tifway'. Under no drought conditions, 'OSU2082' produced a similar amount of inflorescences compared to 'TifTuf' and 'Tahoma31', but produced more inflorescences than 'Tifway'. Under drought stress, 'OSU2082', 'TifTuf', and 'Tifway' produced similar amounts of inflorescences, which were less than 'Tahoma 31'. Under drought stress, 'OSU2082' had the highest percent green color (PGC %), which was greater than 'Tifway', but was not different from 'TifTuf' and 'Tahoma 31'. Without drought stress, the average turfgrass quality rating of 'OSU2082' was not different from 'Tahoma 31' and 'Tifway' but was lower than 'TifTuf'. Under drought stress, the turfgrass quality of 'OSU2082' was not different from 'TifTuf' but was improved over 'Tahoma 31' and 'Tifway'.

The post drought stress recovery of 'OSU2082' was similar to 'TifTuf', which was improved over 'Tahoma 31' and 'Tifway'.

TABLE 4

Turf bermudagrass performance in a field trial at 8 locations in CA, OK, TX, GA, FL, and NC for 2020-2023.

| Entry | Cover (%) | Leaf spot disease | Fall colar | Inflorescences No drought | Inflorescences Drought |
|---|---|---|---|---|---|
| OSU2015 | 52.8 | 4.7 | 2.6 | 3.6 | 2.7 |
| OSU2018 | 62.2 | 3.3 | 4.1 | 3.4 | 1.7 |
| OSU2021 | 60.9 | 6.0 | 3.0 | 3.4 | 1.0 |
| OSU2022 | 66.9 | 8.7 | 3.6 | 4.4 | 2.7 |
| OSU2026 | 65.0 | 4.0 | 3.9 | 2.8 | 2.0 |
| OSU2034 | 62.5 | 5.0 | 4.0 | 3.1 | 1.0 |
| OSU2035 | 70.6 | 6.3 | 3.9 | 3.7 | 1.0 |
| OSU2037 | 46.1 | 6.0 | 2.7 | 1.4 | 1.0 |
| OSU2039 | 43.9 | 6.0 | 2.5 | 2.2 | 1.0 |
| OSU2043 | 65.0 | 7.3 | 3.7 | 5.1 | 4.0 |
| OSU2066 | 57.2 | 8.0 | 2.6 | 5.7 | 1.0 |
| OSU2073 | 72.1 | 7.7 | 4.7 | 4.3 | 2.0 |
| OSU2074 | 60.3 | 8.0 | 2.1 | 4.4 | 1.7 |
| OSU2075 | 65.3 | 5.3 | 3.2 | 5.1 | 2.3 |
| OSU2081 | 73.6 | 8.7 | 4.8 | 2.5 | 1.3 |
| OSU2082 | 70.5 | 8.3 | 4.3 | 4.5 | 1.7 |
| OSU2088 | 67.0 | 6.0 | 4.3 | 5.7 | 3.3 |
| OSU2094 | 67.0 | 8.3 | 2.7 | 4.9 | 6.7 |
| OSU2101 | 59.2 | 8.0 | 3.9 | 6.3 | 4.0 |
| OSU2102 | 53.0 | 5.3 | 3.1 | 4.0 | 1.0 |
| Tahoma31 | 69.1 | 7.3 | 3.3 | 3.9 | 6.0 |
| TifTuf | 78.5 | 8.3 | 5.0 | 4.2 | 1.3 |
| Tifway | 62.4 | 5.7 | 4.0 | 2.7 | 1.0 |
| LSD0.05 | 7.5 | 2.6 | 0.8 | 0.9 | 2.2 |

| Entry | PGC(%) Drought | Re-covery | Spring greenup | Turfgrass quality No drought | Turfgrass quality Drought |
|---|---|---|---|---|---|
| OSU2015 | 61.4 | 4.8 | 3.9 | 4.8 | 4.1 |
| OSU2018 | 71.1 | 5.1 | 4.9 | 5.6 | 4.8 |
| OSU2021 | 59.9 | 5.0 | 4.5 | 5.0 | 4.1 |
| OSU2022 | 51.9 | 4.7 | 4.5 | 5.0 | 3.7 |
| OSU2026 | 57.3 | 5.1 | 4.4 | 5.2 | 4.1 |
| OSU2034 | 58.9 | 5.2 | 3.7 | 5.2 | 4.1 |
| OSU2035 | 70.2 | 5.3 | 4.0 | 5.4 | 4.6 |
| OSU2037 | 46.5 | 4.2 | 4.3 | 4.7 | 3.3 |
| OSU2039 | 25.2 | 2.7 | 3.4 | 4.2 | 3.1 |
| OSU2043 | 51.1 | 5.0 | 4.2 | 5.2 | 4.3 |
| OSU2066 | 45.2 | 3.8 | 2.4 | 4.0 | 3.3 |
| OSU2073 | 94.8 | 6.2 | 4.5 | 5.9 | 5.7 |
| OSU2074 | 82.6 | 4.9 | 2.3 | 4.8 | 4.5 |
| OSU2075 | 88.6 | 5.4 | 4.1 | 5.1 | 4.8 |
| OSU2081 | 92.8 | 6.1 | 4.6 | 5.9 | 5.6 |
| OSU2082 | 94.9 | 5.9 | 4.3 | 5.6 | 5.6 |
| OSU2088 | 81.1 | 5.6 | 4.5 | 5.3 | 4.9 |
| OSU2094 | 90.1 | 5.1 | 4.2 | 5.0 | 4.9 |
| OSU2101 | 58.3 | 3.9 | 4.6 | 5.5 | 4.6 |
| OSU2102 | 43.4 | 4.4 | 4.0 | 5.1 | 3.9 |
| Tahoma31 | 85.7 | 5.2 | 5.4 | 5.7 | 5.0 |
| TifTuf | 89.9 | 6.1 | 5.3 | 6.1 | 5.8 |
| Tifway | 53.1 | 5.0 | 4.3 | 5.6 | 4.7 |
| LSD0.05 | 12.8 | 0.5 | 0.8 | 0.2 | 0.3 |

In 2021 and 2022, the trials at Riverside, CA, Dallas, TX, and Stillwater, OK experienced more lengthy and severe drought conditions than other sites. Turf performance data pulled together over the two years at the three sites are given in Table 5. Results indicated that under severe drought stress, 'OSU2082' had the highest turfgrass quality, with a greater turfgrass quality rating than 'TifTuf', 'Tahoma 31', and 'Tifway' at P<0.10.

TABLE 5

Turfgrass performance at Riverside, CA, Dallas, TX, Stillwater, OK in 2021 and 2022.

| Entry | Inflores-cences Drought | PGC(%) Drought | Re-covery | Turfgrass quality No drought | Turfgrass quality Drought |
|---|---|---|---|---|---|
| OSU2015 | 2.67 | 47.50 | 4.51 | 4.90 | 3.93 |
| OSU2018 | 1.67 | 64.63 | 4.75 | 5.71 | 4.46 |
| OSU2021 | 1.00 | 40.27 | 4.80 | 5.31 | 3.96 |
| OSU2022 | 2.67 | 34.84 | 4.35 | 5.02 | 2.85 |
| OSU2026 | 2.00 | 44.69 | 5.00 | 5.54 | 3.78 |
| OSU2034 | 1.00 | 37.58 | 5.10 | 6.08 | 3.81 |
| OSU2035 | 1.00 | 46.10 | 5.20 | 5.69 | 4.28 |
| OSU2037 | 1.00 | 25.53 | 4.00 | 5.27 | 2.64 |
| OSU2039 | 1.00 | 4.01 | 1.98 | 4.48 | 2.26 |
| OSU2043 | 4.00 | 22.75 | 4.78 | 5.53 | 3.65 |
| OSU2066 | 1.00 | 35.49 | 3.43 | 3.90 | 2.90 |
| OSU2073 | 2.00 | 93.46 | 6.32 | 5.93 | 5.70 |
| OSU2074 | 1.67 | 84.69 | 4.87 | 5.18 | 4.77 |
| OSU2075 | 2.33 | 92.57 | 5.55 | 5.49 | 4.83 |
| OSU2081 | 1.33 | 95.67 | 6.24 | 6.24 | 5.66 |
| OSU2082 | 1.67 | 93.51 | 6.29 | 6.15 | 5.81 |
| OSU2088 | 3.33 | 78.51 | 5.75 | 5.98 | 5.43 |
| OSU2094 | 6.67 | 93.11 | 4.94 | 5.57 | 5.03 |
| OSU2101 | 4.00 | 28.23 | 3.10 | 5.04 | 3.49 |
| OSU2102 | 1.00 | 23.33 | 3.98 | 4.94 | 2.88 |
| Tahoma31 | 6.00 | 84.78 | 4.86 | 5.65 | 4.94 |
| TifTuf | 1.33 | 84.09 | 6.11 | 6.28 | 5.43 |
| Tifway | 1.00 | 29.38 | 4.75 | 5.69 | 3.95 |
| LSD0.05 | 2.17 | 22.21 | 0.62 | 0.54 | 0.43 |
| LSD0.10 | 1.81 | 18.62 | 0.52 | 0.45 | 0.36 |

Shade Tolerance Test

Approximately 40 bermudagrasses were evaluated at two locations (Stillwater, OK and College Station, TX) over four years (2020-2023). Grasses were planted as plugs in mid-July 2020 in Stillwater and mid-August in College Station. Shade was applied in the form of a neutral density poly woven fabric nominally rated to reduce irradiance by 50% (Stillwater) or 63% (College Station) beginning 3 weeks after planting (Stillwater) or 10 weeks after planting (College Station). Turfgrass quality and green coverage were measured monthly during the growing season in 2021-2023 to assess the spread and persistence of plant materials under shade. Data pooled across locations and years indicated 'Tahoma 31' (shade tolerant standard) was the top-performing commercial standard, resulting in a mean quality score of 5.0, while elite lines 'OSU2081' and 'OSU2082' were considered less well-adapted to shade, although comparable to other bermudagrasses in the trial (Table 6). Results suggest that the performance of 'OSU2081' would be improved over 'Tifway' (shade susceptible standard) and that 'OSU2082' would perform similarly to 'Tifway' under shaded conditions.

TABLE 6

Performance of selected bermudagrasses in the SCRI ancillary trait shade trial conducted in Stillwater, OK and College Station, TX from 2020 to 2023.

| Entry | Cover (%) | Spring green up | Turfgrass quality |
|---|---|---|---|
| 'OSU2015' | 46.8 | 2.5 | 3.9 |
| 'OSU2018' | 41.0 | 3.2 | 3.8 |
| 'OSU2021' | 60.1 | 3.2 | 5.4 |

TABLE 6-continued

Performance of selected bermudagrasses in the SCRI ancillary trait shade trial conducted in Stillwater, OK and College Station, TX from 2020 to 2023.

| Entry | Cover (%) | Spring green up | Turfgrass quality |
|---|---|---|---|
| 'OSU2022' | 46.3 | 2.8 | 3.9 |
| 'OSU2026' | 40.8 | 2.2 | 3.4 |
| 'OSU2034' | 43.4 | 2.8 | 3.8 |
| 'OSU2035' | 40.1 | 2.7 | 2.9 |
| 'OSU2037' | 46.0 | 3.7 | 4.1 |
| 'OSU2039' | 36.9 | 3.2 | 2.5 |
| 'OSU2043' | 42.3 | 3.2 | 3.3 |
| 'OSU2066' | 37.9 | 2.6 | 3.2 |
| 'OSU2073' | 40.9 | 3.0 | 3.8 |
| 'OSU2074' | 35.0 | 2.2 | 2.7 |
| 'OSU2075' | 38.9 | 2.7 | 3.3 |
| 'OSU2081' | 46.3 | 3.2 | 4.4 |
| 'OSU2082' | 38.4 | 2.3 | 3.0 |
| 'OSU2088' | 41.5 | 2.3 | 3.7 |
| 'OSU2094' | 38.6 | 2.8 | 3.2 |
| 'OSU2101' | 38.6 | 1.7 | 3.1 |
| 'OSU2102' | 35.3 | 2.3 | 2.6 |
| 'Tahoma 31' | 48.6 | 3.3 | 5.0 |
| 'Tifway' | 38.4 | 2.3 | 3.1 |
| LSD 0.05 | 7.2 | 1.3 | 0.4 |

Sod Harvestability Test

Approximately 40 bermudagrasses were evaluated in Stillwater, OK from 2021 to 2022. Grasses were planted 8 Jul. 2021 from sprigs at 450 bu/acre. Spring green-up and green coverage were measured the year after planting to assess spread. Sod was harvested using a walk behind sod cutter fitted with an 18-inch blade and 1.5-inch depth setting. Sod tensile strength was measured using the device described by Segars et al. (2022) in the horizontal orientation and a digital force meter operated in peak weight model to determine the maximum force at the time of tearing. Raw data were converted using the sod pad width and depth information to reflect the point of sod tensile failure per unit area (kg dm−2). Sod handling quality was assessed on a 1 to 5 visual scale where 1=very poor quality, sod falls apart easily, 2=substantial cracking of sod strip, 3=some cracking of sod pad, this is the suggested minimum quality for harvest of an existing commercial available product, 4=very little cracking, suggested minimum quality for commercialization of new experimental varieties, 5=excellent quality, no cracking of pad (Han, 2009). Data indicate that 'Tahoma 31' and 'TifTuf' had improved spring green-up as compared to 'OSU2081' and 'OSU2082'; however, each genotype grew well and filled in the block at the rating time (Table 7). Sod tensile strength was acceptable for each genotype at 12 months after planting, although sod handling quality varied with 'OSU2081' and 'OSU2082' having inferior quality than 'Tahoma 31'. When harvested at 15 months after planting, 'OSU2082' exhibited inferior sod tensile strength compared to 'Tahoma 31' but was similar to 'TifTuf'. There were no differences at this date for sod handling quality.

TABLE 7

Summary results of selected entries from SCRI sod strength trial in Stillwater, OK.

| | Spring Green Up 11 Apr. 2022 1 to 9 | Green Cover 7 Jun. 2022 % | Sod Tensile Strength 14 Jul. 2022 kg dm$^{-2}$ | Sod Handling Quality 14 Jul. 2022 1 to 5 | Sod Tensile Strength 6 Oct. 2022 kg dm$^{-2}$ | Sod Handling Quality 6 Oct. 2022 1 to 5 |
|---|---|---|---|---|---|---|
| OSU2021 | 5.0b | 70b | 15.1b | 2.7bc | 19.5a | 5.0a |
| OSU2073 | 4.0b | 99a | 27.8ab | 3.0ab | 19.3a | 4.7a |
| OSU2081 | 2.3c | 94a | 34.2a | 2.0c | 15.2ab | 4.7a |
| OSU2082 | 2.7c | 98a | 13.7b | 2.3bc | 7.7b | 4.7a |
| Tahoma 31 | 7.3a | 99a | 20.8ab | 3.7a | 16.7a | 5.0a |
| TifTuf | 6.7a | 99a | 18.3ab | 2.7bc | 10.7ab | 5.0a |

Sod Harvestability On-Farm Tests

'OSU2081' and 'OSU2082' were planted in Yukon, OK in summer 2023. In early December 2023, both 'OSU2081' and 'OSU2082' exhibited adequate sod strength despite the stands being young (observed by the sod farmer), 'OSU2081' sod harvestability was not as good as 'Tahoma 31' and 'OSU2082'. The sod farmer indicated that the 'OSU2081' plot was in a lower area and had not grown as thick as 'OSU2082' and 'Tahoma 31' in the growing season.

Shared Space Planted Nursery (SSPN) Test

This regional field trial was carried out at 7 locations in the southern states (Stillwater, OK; Dallas, TX; Riverside, CA; Tifton and Griffin, GA; Citra, FL; and Jackson Springs, NC). The test included 190 experimental entries ('OSU2081' and 'OSU2082' included) and three standards ('TifTuf', 'Tahoma 31', and 'Tifway'). The nurseries were established using randomized complete block designs with 2 replications in 2020. Since the plots were fully established, the nurseries were not irrigated and managed under natural rainfall conditions. The establishment ratings were collected in 2020 and early 2021, while turf performance data were collected from 2021 to 2023. Data analysis results include selected OSU entries and standard cultivars are presented in Table 8.

'OSU2082' had no differences from the three cultivars in establishment rate and inflorescence prolificacy (Table 8). It had a fall color rating similar to 'Tifway', greater than 'Tahoma 31', but not as high as 'TifTuf'. Its percent green cover (PGC %) under drought conditions was greater than 'Tifway', similar to 'Tahoma 31', but less than 'TifTuf'. Its spring green up was similar to 'Tifway''s but later than 'Tahoma 31' and 'TifTuf''s. Its turfgrass quality was not different from 'Tifway', but lower than 'Tahoma 31' and 'TifTuf' under no drought conditions. Under drought conditions, 'OSU2082' had a quality rating greater than 'Tifway', similar to 'Tahoma 31', but lower than 'TifTuf'.

TABLE 8

Turf bermudagrass performance of OSU selections and three standard cultivars at seven locations over four years (2020-2023).

| Entry | Cover (%) | Leaf spot disease | Fall color | Inflores-cences | PGC(%) Drought |
|---|---|---|---|---|---|

TABLE 8-continued

Turf bermudagrass performance of OSU selections and three standard cultivars at seven locations over four years (2020-2023).

| | | | | | |
|---|---|---|---|---|---|
| OSU2035 | 47.0 | 6.5 | 4.0 | 3.6 | 61.8 |
| OSU2050 | 46.2 | 8.5 | 4.4 | 2.5 | 55.7 |
| OSU2052 | 45.4 | 9.8 | 4.1 | 2.6 | 47.7 |
| OSU2053 | 55.9 | 7.5 | 4.9 | 3.8 | 73.4 |
| OSU2055 | 38.1 | 7.5 | 3.0 | 2.0 | 61.5 |
| OSU2056 | 44.3 | 9.0 | 3.6 | 4.5 | 50.9 |
| OSU2061 | 40.7 | 8.0 | 1.9 | 2.0 | 49.3 |
| OSU2069 | 56.5 | 9.0 | 4.1 | 3.2 | 62.8 |
| OSU2071 | 42.9 | 9.0 | 3.0 | 5.0 | 48.2 |
| OSU2072 | 51.4 | 8.0 | 3.8 | 5.3 | 64 4 |
| OSU2077 | 51.2 | 8.0 | 5.0 | 2.0 | 67.1 |
| OSU2079 | 54.8 | 9.0 | 4.5 | 2.6 | 62.4 |
| OSU2081 | 57.6 | 9.0 | 5.6 | 2.6 | 73.2 |
| OSU2082 | 56.2 | 9.0 | 4.5 | 3.4 | 55.1 |
| OSU2083 | 43.4 | 8.5 | 1.9 | 1.7 | 55.2 |
| OSU2087 | 49.4 | 8.5 | 5.0 | 3.6 | 68.0 |
| OSU2090 | 47.5 | 9.0 | 3.2 | 4.1 | 60.4 |
| OSU2093 | 50.5 | 8.0 | 3.7 | 4.5 | 55.4 |
| OSU2100 | 45.4 | 9.0 | 4.3 | 2.9 | 64.3 |
| Tahoma31 | 50.4 | 8.0 | 3.0 | 3.7 | 56.8 |
| TifTuf | 66.8 | 9.0 | 5.5 | 4.1 | 79.3 |
| Tifway | 49.9 | 4.5 | 3.5 | 3.4 | 46.6 |
| LSD0.05 | 10.5 | 2.3 | 0.9 | 1.8 | 16.7 |

TABLE 8-continued

Turf bermudagrass performance of OSU selections and three standard cultivars at seven locations over four years (2020-2023).

| | | | Turfgrass quality | |
|---|---|---|---|---|
| Entry | Re-covery | Spring greenup | No drought | Drought |
| OSU2035 | 5.4 | 4.6 | 5.4 | 4.2 |
| OSU2050 | 6.0 | 4.2 | 5.2 | 4.6 |
| OSU2052 | 5.0 | 4.2 | 5.2 | 4.4 |
| OSU2053 | 5.9 | 4.8 | 5.6 | 4.8 |
| OSU2055 | 6.3 | 2.7 | 5.5 | 5.2 |
| OSU2056 | 5.3 | 3.9 | 5.2 | 4.2 |
| OSU2061 | 5.4 | 2.2 | 4.8 | 4.3 |
| OSU2069 | 5.9 | 4.3 | 5.5 | 4.7 |
| OSU2071 | 5.7 | 3.7 | 4.8 | 4.5 |
| OSU2072 | 5.3 | 3.3 | 5.1 | 4.2 |
| OSU2077 | 5.9 | 4.4 | 5.8 | 5.2 |
| OSU2079 | 5.9 | 4.3 | 5.7 | 4.7 |
| OSU2081 | 6.5 | 4.9 | 6.2 | 5.7 |
| OSU2082 | 5.2 | 4.0 | 5.4 | 4.6 |
| OSU2083 | 5.0 | 2.3 | 4.3 | 4.0 |
| OSU2087 | 5.9 | 4.2 | 5.5 | 4.6 |
| OSU2090 | 5.4 | 3.5 | 4.9 | 4.1 |
| OSU2093 | 5.6 | 4.1 | 5.1 | 4.2 |
| OSU2100 | 5.5 | 4.4 | 5.1 | 4.6 |
| Tahoma31 | 5.1 | 5.3 | 5.8 | 4.1 |
| TifTuf | 5.9 | 5.1 | 6.3 | 5.6 |
| Tifway | 5.0 | 4.3 | 5.1 | 3.8 |
| LSD0.05 | 0.8 | 1.0 | 0.3 | 0.6 |

What is claimed is:

1. A new and distinct Bermudagrass plant named 'OSU2082' substantially as described and illustrated herein.

* * * * *